United States Patent [19]

Kurahashi et al.

[11] Patent Number: 4,710,518
[45] Date of Patent: Dec. 1, 1987

[54] NOVEL N-BENZYL-CYCLOPROPANECARBOXAMIDE FUNGICIDES

[75] Inventors: Yoshio Kurahashi, Tokyo; Kozo Shiokawa, Kanagawa; Shinzo Kagabu, Tokyo; Shinji Sakawa, Tokyo; Koichi Moriya, Tokyo, all of Japan

[73] Assignee: Nihon Tokushu Noyaku Seizo K.K., Tokyo, Japan

[21] Appl. No.: 850,462

[22] Filed: Apr. 9, 1986

Related U.S. Application Data

[63] Continuation-in-part of Ser. No. 750,558, Jun. 27, 1985, abandoned.

[30] Foreign Application Priority Data

Jul. 2, 1984 [JP] Japan ............................ 59-135268
Jul. 6, 1984 [JP] Japan ............................ 59-138955
Nov. 13, 1985 [JP] Japan ............................ 60-252822

[51] Int. Cl.⁴ ............... C07C 103/737; C07C 61/15; A01N 37/18
[52] U.S. Cl. ......................... 514/624; 564/190; 260/544 F; 260/544 L; 562/506
[58] Field of Search ................... 564/190; 514/624

[56] References Cited

U.S. PATENT DOCUMENTS

3,277,107 10/1966 Neighbors et al. ............... 71/118 X
3,277,171 10/1966 Hopkins et al. .................. 564/190
4,274,862 6/1981 Kirino et al. ..................... 71/118 X

FOREIGN PATENT DOCUMENTS

58-26847 2/1983 Japan .
1331706 4/1972 United Kingdom .

OTHER PUBLICATIONS

Pilgram et al, J. Agric. Food Chem., 1982, 30, pp. 971-977.

*Primary Examiner*—Charles F. Warren
*Assistant Examiner*—Carolyn S. Greason
*Attorney, Agent, or Firm*—Sprung Horn Kramer & Woods

[57] ABSTRACT

Novel fungicidally active N-benzyl-cyclopropanecarboxamides of the formula

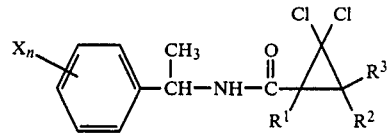

wherein
X represents halogen,
n represents 1 or 2,
$R^1$ represents hydrogen, halogen or lower alkyl,
$R^2$ represents lower alkyl, halogen-substituted lower alkyl or hydrogen, and
$R^3$ represents hydrogen or lower alkyl.

The acid components thereof, other than when $R^1$ is hydrogen or alkyl and $R^2$ is hydrogen or alkyl, are also new.

10 Claims, No Drawings

NOVEL N-BENZYL-CYCLOPROPANECARBOXAMIDE FUNGICIDES

This application is a continuation-in-part of Ser. No. 750,558 filed on June 27, 1985.

The invention relates to novel N-benzyl-cyclopropanecarboxamide derivatives, a process for production thereof, intermediates thereof, and their use as agricultural and horticultural fungicides.

The specification of Japanese Laid-Open Patent Publication No. 66555/1980 known before the filing date of the present application states that N-benzyl-acetamide derivates represented by the following general formula

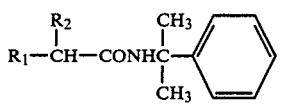

wherein
$R_1$ represents hydrogen or lower alkyl,
$R_2$ represents alkyl or cycloalkyl or
$R_1$ and $R_2$ may together form a ring,
have herbicidal activity. The specification describes a compound of the following formula:

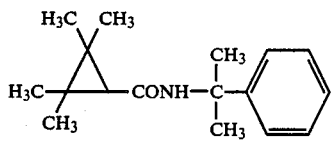

The above general formula (A) does not encompass the compounds of general formula (I) specified in the present invention. Moreover, the above-cited patent document does not at all refer to fungicide applications.

The specification of Japanese Laid-Open Patent Publication No. 26847/1983 known before the filing date of the present application states that N-benzyl-acetamide derivatives represented by the general formula

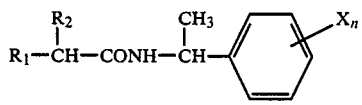

wherein
$R_1$ represents alkyl branched at the alpha-position,
$R_2$ represents hydrogen, lower alkyl or lower alkenyl or
$R_1$ and $R_2$ together may represent an alkylene group,
X represents halogen, lower alkyl, lower alkoxy, cyano or nitro, and
n is an integer of 1 to 3,
have fungicidal activity in agriculture and horticulture. The specification describes a compound of the following formula

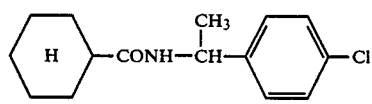

However, the action of these compounds is not always completely satisfactory in all fields of use, particularly when small amounts and concentrations are used.

New N-benzyl-cyclopropanecarboxamide derivatives of the following formula (I)

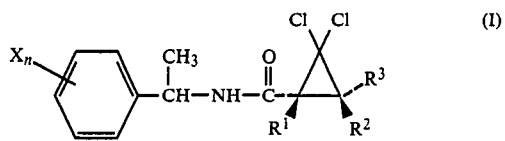

wherein
X represents halogen,
n represents 1 or 2,
$R^1$ represents hydrogen, halogen or lower alkyl,
$R^2$ represents hydrogen, lower alkyl or halogen-substituted lower alkyl and
$R^3$ represents hydrogen or lower alkyl,
have been found.

Furthermore, it has been found that the N-benzyl-cyclopropanecarboxamide derivatives of the formula (I)

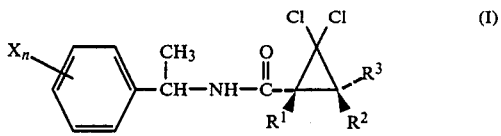

wherein
X represents halogen,
n represents 1 or 2,
$R^1$ represents hydrogen, halogen or lower alkyl,
$R^2$ represents hydrogen, lower alkyl or halogen-substituted lower alkyl and
$R^3$ represents hydrogen or lower alkyl,
are obtained if amino compounds of the formula (II)

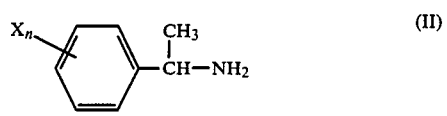

wherein x and n are as defined above, are reacted with a compound represented by the general formula

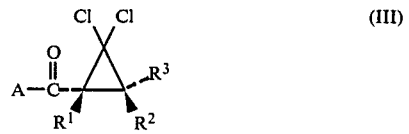

wherein
each of $R^1$, $R^2$ and $R^3$ is as defined above, and
A represents hydroxy or halogen,
if appropriate in the presence of a diluent and, if appropriate, in the presence of an acid binder.

The new N-benzyl-cyclopropanecarboxamide derivatives of the formula (I) have, in particular, fungicidal properties. It has been found that the compounds of this invention exhibit an excellent controlling efficacy especially suitable for the purpose of controlling plant diseases, and particularly exhibits an outstanding efficacy most suitable for the control of rice blast (*Pyricularia oryzae*). This controlling efficacy is much better than the efficacies of compounds having an analogous chemical structure, for example the compounds of formulae (A-1) and (B-1) described in the known publications.

The compounds according to the invention thus represent an enrichment of the art.

Formula (I) gives a general definition of the N-benzyl-cyclopropanecarboxamide derivatives according to the invention. Preferred compounds of the formula (I) are those in which X represents halogen as fluoro, chloro, bromo and iodo,
n represents 1 or 2,
R$^1$ represents hydrogen, halogen as exemplified above or alkyl with 1 to 4 carbon atoms such as methyl, ethyl, n-propyl, iso-propyl or n-, sec.-, iso- and tert.-butyl,
R$^2$ represents hydrogen, alkyl as exemplified above and halogen substituted alkyl with 1 to 4 carbon atoms and 1 to 5 halogen atoms, alkyl and halogen as exemplified above, for example, mono-(di- or tri-)chloromethyl, mono-(di- or tri-)fluoromethyl, mono-(di- or tri-)bromomethyl, 1-(or 2-)chloro(bromo or fluoro)ethyl, 1,1-(1,2 or 2,2)di-chloro(bromo or fluoro)ethyl, and 1,1,1-(1,1,2-, 1,2,2- or 2,2,2-)-trichloro(bromo or fluoro)ethyl and
R$^3$ represents hydrogen or lower alkyl with 1 to 4 carbon atoms such as exemplified above.

Particularly preferred compounds are those of the general formula (I), in which
X represents fluoro, chloro or bromo,
n represents 1 or 2,
R$^1$ represents hydrogen, methyl, ethyl, n-propyl, iso-propyl, chloro, bromo or fluoro,
R$^2$ represents hydrogen, methyl, ethyl, n-propyl, iso-propyl, n-butyl, tert.-butyl, sec.-butyl, iso-butyl, chloromethyl, bromomethyl, trifluoromethyl, 2,2,2-trifluoroethyl or 2-chloroethyl, and
R$^3$ represents hydrogen, methyl or ethyl.

If, for example, 4-chloro-α-methylbenzylamine and 1,2,2-trichloro-3-methyl-(cis)-3-methyl-cyclopropane carboxylic acid chloride are used as starting materials, the course of the reaction of the process according to the invention can be represented by the following equation:

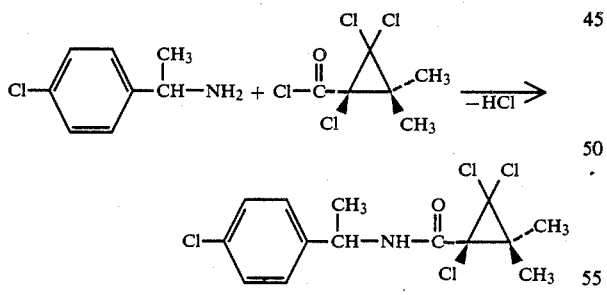

Formula (II) gives a general definition of the amino compounds which are required as starting materials for carrying out the process according to the invention. In this formula, X and n have the same meanings which are given in the description of the compounds of the formula (I).

The compounds of formula (II) are known. Specific examples of starting compounds of formula (II) include, for example, 4-chloro-, 4-fluoro-, 4-bromo-, 2-chloro-, 3,4-dichloro- and 2,6-dichloro-α-methylbenzylamine.

Formula (III) gives a general definition of the cyclopropanecarboxylic acid derivatives which are required as starting materials for carrying out the process according to the invention. In this formula, R$^1$, R$^2$ and R$^3$ have the same meanings which are given in the description of the compounds of the formula (I) and A preferably represents hydroxy or halogen, such as chloro and bromo.

Specific examples of the compound of general formula (III) which is likewise a starting material are 2,2-dichloro-(trans)-3-chloromethyl-(cis)-3-methylcyclopropanecarboxylic acid, 1,2,2-trichloro-3,3-dimethylcyclopropanecarboxylic acid, 1,2,2-trichloro-3,3-diethylcyclopropanecarboxylic acid, 2,2-dichloro-(trans)-3-bromomethyl-(cis)-3-methylcyclopropanecarboxylic acid, 2,2-dichloro-(trans)-3-trifluoromethyl-(cis)-3-methylcyclopropanecarboxylic acid, 1-bromo-2,2-dichloro-3,3-dimethylcyclopropanecarboxylic acid, 2,2-dichloro-1-fluoro-3,3-dimethylcyclopropanecarboxylic acid, 2,2-dichloro-(trans)-3-(2,2,2-trifluoroethyl)-(cis)-3-methylcyclopropanecarboxylic acid and 2,2-dichloro-(trans)-3-(2-chloroethyl)-(cis)-3-methylcyclopropanecarboxylic acid, 2,2-dichloro-1-methylcyclopropanecarboxylic acid, 2,2-dichloro-1-ethylcyclopropanecarboxylic acid, 2,2-dichloro-(trans)-3-methylcyclopropanecarboxylic acid, 2,2-dichloro-1-methyl-(trans)-3-methylcyclopropanecarboxylic acid, 2,2-dichloro-1-ethyl-(trans)-3-ethylcyclopropanecarboxylic acid, 2,2-dichloro-3,3-dimethylcyclopropanecarboxylic acid, 2,2-dichloro-3,3-diethylcyclopropanecarboxylic acid, and 2,2-dichloro-1,3,3-trimethylcyclopropanecarboxylic acid. Halides, such as chlorides and bromides, of these carboxylic acids may also be cited as examples. Some of the cyclopropanecarboxylic acid derivatives of the formula (III) are known.

Compounds which are not yet known are those of the formula (IIIa)

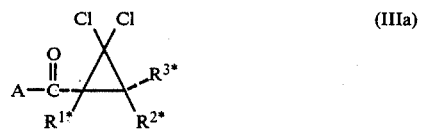

wherein
R$^{1*}$ represents hydrogen, halogen or alkyl and
R$^{2*}$ represents lower alkyl or halogen-substituted lower alkyl, provided that when R$^{1*}$ is a hydrogen or alkyl atom, R$^{2*}$ represents halogen-substituted lower alkyl,
R$^{3*}$ represents lower alkyl, and
A represents hydroxyl or halogen such as chloro or bromo.

Preferred compounds of the formula (IIIc) are those in which
R$^{1*}$ represents hydrogen, halogen, as fluoro, chloro, bromo or iodo or alkyl with 1 to 4 carbon atoms such as methyl, ethyl, n-propyl, iso-propyl or n-, sec.-, iso- and tert.-butyl,
R$^{2*}$ represents alkyl as exemplified above or halogen-substituted alkyl with 1 to 4 carbon atoms and 1 to 5 halogen atoms, alkyl and halogen as exemplified above, for example, mono-(di- or tri-)chloromethyl, mono-(di- or tri-)fluoromethyl, mono-(di- or tri-)bromomethyl, 1-(or 2-)-chloro(bromo, or fluoro)ethyl, 1,1-(1,2 or 2,2)di-chloro (bromo or fluoro)ethyl, and 1,1,1-(1,1,2-, 1,2,2- or 2,2,2-)-tri-chloro(bromo or fluoro)ethyl, provided that when R$^{1*}$ is hydrogen or alkyl, R$^{2*}$ represents halogen-substituted lower alkyl, $R^{3*}$ represents lower alkyl with 1 to 4 carbon atoms such as exemplified above, and A represents hydroxyl or halogen such as chloro or bromo.

Particularly preferred compounds are those of the general formula (IIIa), in which $R^{1*}$ represents hydrogen, methyl, ethyl, n-propyl, iso-propyl, chloro, bromo or fluoro, $R^{2*}$ represents methyl, ethyl, n-propyl, iso-propyl, n-butyl, tert.-butyl, sec.-butyl, iso-butyl, chloromethyl, bromomethyl, tri-fluoromethyl, 2,2,2-trifluoroethyl or 2-chloroethyl, provided that when $R^{1*}$ is hydrogen or alkyl as exemplified above, $R^{2*}$ represents halogen-substituted lower alkyl as exemplified, $R^{3*}$ represents methyl or ethyl and A has the above given meaning.

The compounds of general formula (IIIa) in accordance with this invention can be easily produced, for example, by the following processes:

Process i

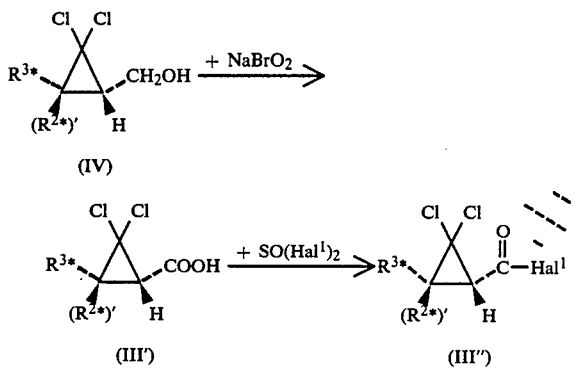

In the formula, $(R^{2*})$ represents halogen-substituted lower alkyl, and $Hal^1$ represents halogen and $R^{3*}$ has the meaning above.

Process ii

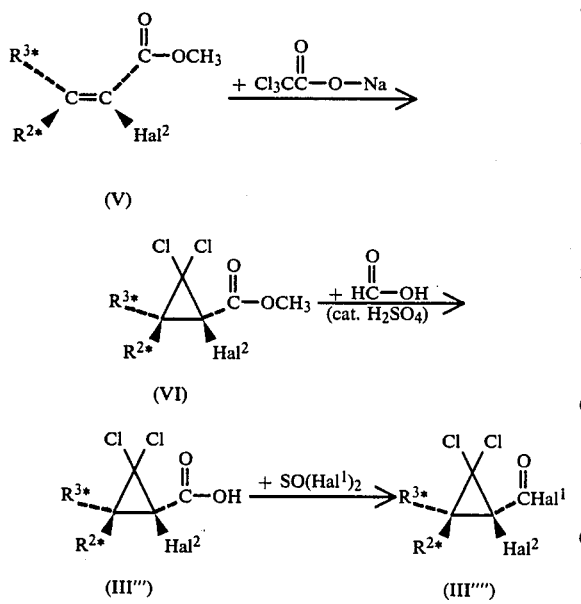

In the formulae, $R^{2*}$, $R^{3*}$ and $Hal^1$ are as defined above, and $Hal^2$ represents a halogen atom.

Specific examples of the compound of general formula (IV) which is the starting material in process i) include 2,2-dichloro-(trans)-3-chloromethyl-(cis)-3-methylcyclopropanemethanol, 2,2-dichloro-(trans)-3-bromomethyl-(cis)-3-methylcyclopropanemethanol, 2,2-dichloro-(trans)-3-trifluoromethyl-(cis)-3-methylcyclopropanemethanol, 2,2-dichloro-(trans)-3-(2,2,2-trifluoroethyl)-(cis)-3-methylcyclopropanemethanol, and 2,2-dichloro-(trans)-3-(2-chloroethyl-(cis)-3-methycyclopropanemethanol.

Specific examples of the compound of general formula (V) which is the starting material in process ii) are methyl 2-chloro-crotonate, methyl 2-bromo-crotonate, methyl 2-fluoro-crotonate and methyl 2-chloro-3-ethyl-2-pentenoate. Instead of the methyl esters of general formula (V), other corresponding alkyl esters may also be cited.

Instead of sodium trichloroacetate to be reacted with the compound of general formula (V) in process ii), 50% sodium hydroxide and a phase transfer catalyst such as triethyl benzyl ammonium chloride in chloroform may be used.

By citing the following typical examples, processes i) and ii) will be described.

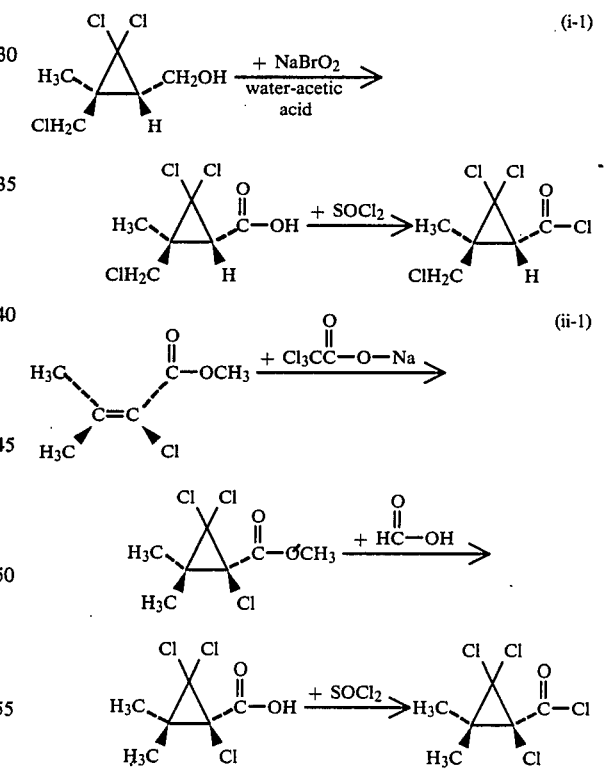

To perform the above processes, the same inert solvents or diluents as mentioned later and which are used to produce the products of formula (I) may be used.

These processes i) and ii) can be carried out over a wide temperature range, for example at a temperature of from about $-20°$ C. to the boiling point of the mixture, desirably at a temperature between about $0°$ to about $100°$ C. Desirably, the processes are carried out under atmospheric pressure, but is also possible to operate under elevated or reduced pressure.

The process according to the invention can be carried out desirably by using a solvent or a diluent. For this purpose, all inert solvents or diluents can be used.

Examples of such solvents or diluents include water; aliphatic, alicyclic and aromatic hydrocarbons (which may optionally be chlorinated) such as hexane, cyclohexane, petroleum ether, ligroin, benzene, toluene, xylene, methylene chloride, chloroform, carbon tetrachloride, ethylene chloride, trichloroethylene and chlorobenzene; ethers such as diethyl ether, methyl ethyl ether, diisopropyl ether, dibutyl ether, propylene oxide, dioxane and tetrahydrofuran; ketones such as acetone, methyl ethyl ketone, methyl isopropyl ketone and methyl isobutyl ketone; nitriles such as acetonitrile, propionitrile and acrylonitrile; esters such as ethyl acetate and amyl acetate; acid amides such as dimethylformamide and dimethylacetamide; sulfones and sulfoxides such as dimethyl sulfoxide and sulfolane.

The above final reaction may be carried out in the presence of an acid binder. Examples of the acid binder include the hydroxides, carbonates, bicarbonates and alcoholates of alkali metals and tertiary amines such as triethylamine, diethylaniline and pyridine, all of which are generally used.

When the carboxylic acid is used as the starting material of general formula (III) in the above process, a dehydrocondensing agent can be used. An example is N,N'-dicyclohexyl carbodiimide.

The above process can be carried out over a wide temperature range. Generally, it can be carried out at a temperature between about $-20°$ C. and the boiling point of the mixture, desirably between about $0°$ C. and about $100°$ C. Desirably, the reaction is carried out under normal atmospheric pressure, but it is also possible to operate under elevated or reduced pressures.

The compounds of this invention can be safely used without causing phytotoxicity to plants. They exhibit an excellent controlling efficacy on a broad range of plant diseases in addition to rice blight and have an excellent residual effect. Hence, they can be applied advantageously and conveniently for controlling a broad range of plant diseases.

The fungicidal spectrum of the compounds of this invention shows that they can be effectively used against plant diseases induced by Archimycetes, Phycomycetes, Ascomycetes, Basidiomycetes, Fungi Imperfecti, and bacteria.

Typical examples of the fungicidal spectrum of the compounds of this invention are rice blast (*Pyricularia oryzae*) and anthracnose on cucumber, melon and the like (*Colletotrichum laqenarium*). The fungicidal spectrum range is not limited to them, however.

As an agricultural and horticultural fungicide, the compounds of formula (I) in accordance with this invention may be used directly upon dilution with water, or in various formulations obtained by methods generally practiced in the production of agricultural chemicals using agriculturally acceptable adjuvants. In actual use, these various formulations may be applied directly or after diluting them with water to the desired concentrations.

The agriculturally acceptable adjuvants as referred to herein include, for example, diluents (solvents, extenders, carriers), surface-active agents (solubilizing agents, emulsifiers, dispersing agents, wetting agents), stabilizers, stickers, aerosol propellants and synergists.

Examples of the solvents are water, and organic solvents, for example hydrocarbons [such as n-hexane, petroleum ether, petroleum fractions (e.g., paraffin waxes, kerosene, light oils, middle oils and heavy oils), benzene, toluene, and xylene], halogenated hydrocarbons (such as methylene chloride, carbon tetrachloride, ethylene chloride, ethylene dibromide, chlorobenzene and chloroform), alcohols (such as methanol, ethanol, propanol and ethylene glycol), ethers (such as diethyl ether, ethylene oxide and dioxane), alcohol ethers (such as ethylene glycol monomethyl ether), ketones (such as acetone and isophorone), esters (such as ethyl acetate and amyl acetate), amides (such as dimethylformamide and dimethylacetamide) and sulfoxides (such as dimethyl sulfoxide).

Examples of the extenders or carriers include inorganic powders, for example sulfur, slaked lime, magnesium lime, gypsum, calcium carbonate, silica, perlite, pumice, calcite, diatomaceous earth, amorphous silica, alumina, zeolites, and clay minerals (such as pyrophyllite, talc, montmorillonite, beidellite, vermiculite, kaolinite and mica); vegetable powers such as cereal powders, starches, processed starches, sugar, glucose and crushed stalks of plants; and powders of synthetic resins such as phenolic resins, urea resins, and vinyl chloride resins.

Examples of the surface-active agents include anionic surface-active agents such as alkylsulfonic acid esters (such as sodium laurylsulfate), arylsulfonic acids (such as alkylarylsulfonic acid salts and sodium alkylnaphthalenesulfonates), succinic acid salts, and salts of sulfuric acid esters of polyethylene glycol alkylaryl ethers; cationic surface-active agents such as alkylamines (e.g., laurylamine, stearyl trimethyl ammonium chloride and alkyl dimethylbenzyl ammonium chloride) and polyoxyethylene alkylamines; nonionic surface-active agents such as polyoxyethylene glycol ethers (e.g., polyoxyethylene alkylaryl ethers and the condensation products thereof), polyoxyethylene glycol esters (e.g., polyoxyethylene fatty acid esters), and polyhydric alcohol esters (e.g., polyoxyethylene sorbitan monolaurate); and amphoteric surface-active agents.

Examples of other adjuvants include stabilizers; stickers (such as agricultural soaps, casein lime, sodium alginate, polyvinyl alcohol, vinyl acetate-type adhesives and acrylic adhesives); aerosol propellants (such as trichlorofluoromethane, dichlorofluoromethane, 1,2,2-trichloro-1,1,2-trifluoroethane, chlorobenzene, LNG, and lower ethers); combustion controlling agents for fumigants (such as nitrites, zinc powder, and dicyandiamide); oxygen-yielding agents (such as chlorates); effect-prolonging agents; dispersion stabilizers [such as casein, tragacanth, carboxymethyl cellulose (CMC), and polyvinyl alcohol (PVA)]; and synergists.

The compounds of this invention can be formulated into various forms by methods generally practiced in the production of agricultural chemicals. Illustrative of such forms are emulsifiable concentrates, oil preparations, wettable powders, soluble powders, suspensions, dust, granules, pulverulent preparations, fumigants, tablets, aerosols, pastes and capsules.

The agricultural and horticultural fungicide of this invention may contain about 0.1 to about 95% by weight, preferably about 0.5 to about 90% by weight, of the aforesaid active ingredient.

In actual use, the suitable amount of the active compound in the aforesaid various formulations and ready-to-use preparations is generally about 0.0001 to about 20% by weight, preferably about 0.005 to about 10% by weight.

The content of the active ingredient can be properly varied depending upon the type of the formulation, the method, purpose, time and locus of its application, the state of occurrence of diseases.

If required, the compounds of this invention may be used in combination with other agricultural chemicals, for example insecticides, other fungicides, miticides, nematocides, antiviral agents, herbicides, plant growth regulators and attractants [such as organophosphate compounds, carbamate compounds, dithio (or thiol) carbamate compounds, organochlorine compounds, dinitro compounds, organosulfur or organometallic compounds, antibiotics, substituted diphenyl ether compounds, urea compounds, and triazine compounds], and/or fertilizers.

Various formulations and ready-to-use preparations containing the aforesaid active ingredient of the invention can be applied by various methods generally practiced in the field of agricultural chemical application, for example spraying (liquid spraying, misting, atomizing, dusting, granule scattering, water surface application, pouring, etc.); soil application (mixing, sprinkling, vaporing and pouring etc.), surface application (such as coating, banding, dust coating and covering); and dipping. It can also be used by the so-called ultralow volume spraying method. According to this method, the active ingredient may be included in an amount of 100%.

The rate of application per unit area can be properly chosen, and is, for example, about 0.03 to about 10 kg, preferably about 0.3 to about 6 kg, per hectare. In special cases, however, it may, and sometimes should, be outside the specified range.

According to this invention, there can be provided an agricultural and horticultural fungicidal composition comprising the compound of general formula (I) as an active ingredient and a diluent (a solvent and/or an extender and/or a carrier) and/or a surface-active agent, and if further required, a stabilizer, a sticker, and a synergist.

This invention also provides a method for controlling a crop disease, which comprises applying to a pathogen and/or the locus of its occurence and/or the locus of occurrence of a crop disease, the compound of general formula (I) either singly or in admixture with a diluent (a solvent and/or an extender and/or a carrier) and/or a surface-active agent and if further required, a stabilizer, a sticker and a synergist.

The following examples illustrate the present invention specifically, it should be noted however that the invention is not limited to these specific examples alone.

SYNTHESIS OF INTERMEDIATES

Example (a)

Eight grams of 2,2-dichloro-(trans)-3-chloromethyl-(cis)-3-methylcyclopropanemethanol was suspended in a mixed solvent of acetic acid (30 ml) and water (6 ml), and 16 g of sodium bromite hydrate (about 60% as sodium bromite) was added at room temperature. After the addition, the reaction temperature was raised to 40° C. After performing the reaction for a total period of 8 hours, the reaction mixture was poured into ice water, adjusted to pH 5 with dilute hydrochloric acid, and extracted with ether. The ethereal layer was washed with an aqueous solution of sodium thiosulfate and dried over anhydrous sodium sulfate. Ether was evaporated under reduced pressure, and the residue was recrystallized from hexane to give the desired 2,2-dichloro-(trans)-3-chloromethyl-(cis)-3-methylcyclopropanecarboxylic acid (3.2 g) represented by the followiing formula. mp. 118°–120° C.

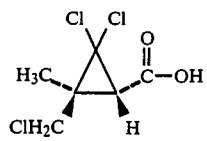

(Compound No. III-a)

Example (b)

Compound No. III-a (3.0 g) synthesized in Example (a) was reacted with thionyl chloride (1.0 ml) at 60° C. Distillation of the reaction mixture under reduced pressure gave the desired 2,2-dichloro-(trans)-chloromethyl-(cis)-3-methylcyclopropanecarboxylic acid chloride (2.8 g) represented by the following formula. mp. 105°–107° C./20 mmHg.

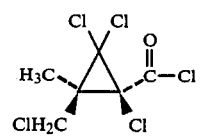

(Compound No. III-b)

By the same method as in Example (a) or (b), the compounds of general formula (III) in accordance with this invention which are shown in Table 1 were synthesized.

TABLE 1

| Compound No. | General formula (III) | Method |
|---|---|---|
| III-c | Cl, Cl, H₃C, BrH₂C, H, C–OH | Example (a) |
| III-d | Cl, Cl, H₃C, BrH₂C, H, C–Cl | Example (b) |
| III-e | Cl, Cl, H₃C, F₃C, H, C–OH | Example (a) |
| III-f | Cl, Cl, H₃C, F₃C, H, C–Cl | Example (b) |
| III-g | Cl, Cl, H₃C, F₃CH₂C, H, C–OH | Example (a) |
| III-h | Cl, Cl, H₃C, F₃CH₂C, H, C–Cl | Example (b) |

TABLE 1-continued

| Compound No. | General formula (III) | Method |
|---|---|---|
| III-i | H₃C, ClH₂CH₂C — cyclopropane — Cl, Cl, C(=O)OH, H | Example (a) |
| III-j | H₃C, ClH₂CH₂C — cyclopropane — Cl, Cl, C(=O)Cl, H | Example (b) |

Example (k)

Methyl 1,2,2-trichloro-3,3-dimethylcyclopropanecarboxylate (10 g) was dissolved in formic acid (20 ml), and concentrated sulfuric acid (0.1 g) was added. The mixture was gently heated under reflux for 12 hours. After cooling, water (60 ml) was added to the reaction mixture. The precipitated crystals were collected by filtration, and recrystallized from hexane to give the desired 1,2,2-trichloro-3,3-dimethylcyclopropanecarboxylic acid (3.4 g) represented by the following formula. mp. 148°–150° C.

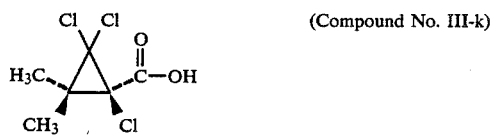

(Compound No. III-k)

Example (l)

The 1,2,2-trichloro-2,2-dimethylcyclopropanecarboxylic acid (3.0 g) synthesized in Example (k) and thionyl chloride (1.0 ml) were mixed, and reacted at 60° C. The reaction mixture was distilled under reduced pressure to give the desired 1,2,2-trichloro-3,3-dimethylcyclopropanecarboxylic acid chloride (2.8 g) represented by the following formula.

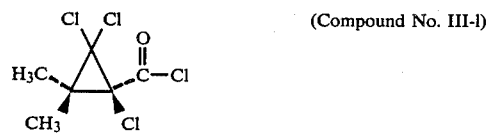

(Compound No. III-l)

Example (m)

The compounds of general formula (III) in accordance with this invention which are shown in Table 2 were synthesized by the same method as in Example (k) or (l).

TABLE 2

| Compound No. | General formula (III) | Method |
|---|---|---|
| III-m | H₅C₂, H₅C₂ — cyclopropane — Cl, Cl, C(=O)OH, Cl | Example k |
| III-n | H₅C₂, H₅C₂ — cyclopropane — Cl, Cl, C(=O)Cl, Cl | Example l |
| III-o | H₃C, CH₃ — cyclopropane — Cl, Cl, C(=O)OH, Br (mp. 150~152° C.) | Example k |
| III-p | H₃C, CH₃ — cyclopropane — Cl, Cl, C(=O)Cl, Br (bp. 113~116° C./20 mmHg) | Example l |
| III-q | H₃C, CH₃ — cyclopropane — Cl, Cl, C(=O)OH, F | Example k |
| III-r | H₃C, CH₃ — cyclopropane — Cl, Cl, C(=O)Cl, F | Example l |
| III-s | H₃C, ClH₂C — cyclopropane — Cl, Cl, C(=O)OH, Cl | Example k |
| III-t | H₃C, ClH₂C — cyclopropane — Cl, Cl, C(=O)Cl, Cl | Example l |

COMPOUNDS OF FORMULA (I)

Example 1

4-Chloro-α-methylbenzylamine (15.6 g) and triethylamine (10.1 g) were dissolved in toluene (150 ml). With stirring, a solution of 1,2,2-trichloro-3,3-dimethylcyclopropanecarboxylic acid chloride (23.6 g) in toluene (30 ml) was added dropwise to the solution at 0° to 10° C. After the addition, the mixture was stirred at room temperature for 2 hours. The reaction mixture was poured into ice water, and the aqueous layer was extracted with toluene. The toluene layers were combined, washed with a 1% aqueous solution of hydrochloric acid, a 1% aqueous solution of sodium hydroxide and water in this order, and then dried over anhydrous sodium sulfate. Toluene was evaporated under reduced pressure to give the desired N-(4-chloro-α-methylbenzyl)-1,2,2-trichloro-3,3-dimethylcyclopropanecarboxamide (32 g) represented by the following formula as colorless crystals. mp. 138°–139° C.

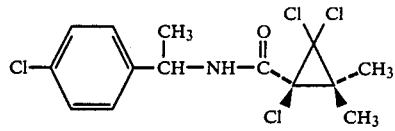 (Compound No. 1)

Compounds of this invention synthesized in accordance with the same method as above are shown in Table 3 below.

TABLE 3

| Compound No. | Compound of this invention |
|---|---|
| 2 | N—(4-chloro-α-methylbenzyl)-2,2-dichloro-(trans)-3-chloromethyl-(cis)-3-methylcyclopropanecarboxamide (mp. 138–141° C.) |
| 3 | N—(4-chloro-α-methylbenzyl)-1,2,2-trichloro-3,3-diethylcyclopropanecarboxamide |
| 4 | N—(4-chloro-α-methylbenzyl)-2,2-dichloro-(trans)-3-bromomethyl-(cis)-3-methylcyclopropanecarboxamide |
| 5 | N—(4-(chloro-α-methylbenzyl)-2,2-dichloro-(trans)-3-trifluoromethyl-(cis)-3-methylcyclopropanecarboxamide |
| 6 | N—(4-chloro-α-methylbenzyl)-1-bromo-2,2-dichloro-3,3-dimethylcyclopropanecarboxamide (mp. 142~144° C.) |
| 7 | N—(4-chloro-α-methylbenzyl)-2,2-dichloro-1-fluoro-3,3-dimethylcyclopropanecarboxamide |
| 8 | N—(4-fluoro-α-methylbenzyl)-1,2,2-trichloro-3,3-dimethylcyclopropanecarboxamide |
| 9 | N—(3,4-dichloro-α-methylbenzyl)-1,2,2-trichloro-3,3-dimethylcyclopropanecarboxamide |
| 10 | N—(4-bromo-α-methylbenzyl)-1,2,2-trichloro-3,3-dimethylcyclopropanecarboxamide |
| 11 | N—(4-chloro-α-methylbenzyl)-2,2-dichloro-(trans)-3-(2,2,2-trifluoroethyl)-(cis)-3-methylcyclopropanecarboxamide |
| 12 | N—(4-chloro-α-methylbenzyl)-2,2-dichloro-(trans)-3-(2-chloroethyl)-(cis)-3-methylcyclopropanecarboxamide |
| 13 | N—(4-chloro-α-methylbenzyl)-1,2,2-trichloro-(trans)-3-chloromethyl-(cis)-3-methylcyclopropanecarboxamide |

Example 14

4-Chloro-α-methylbenzylamine (15.6 g) and triethylamine (10.1 g) were dissolved in toluene (150 ml), and with stirring, a solution of 2,2-dichloro-1-methyl-(trans)-3-methylcyclopropanecarboxylic acid chloride (20.2 g) in toluene (30 ml) was added dropwise at 0° to 10° C. After the addition, the mixture was stirred at room temperature for 2 hours. The reaction mixture was poured onto ice water, and the aqueous layer was washed with toluene. The toluene layers were combined, and washed with a 1% aqueous solution of hydrochloric acid, a 1% aqueous solution of sodium hydroxide, and water in this order, and dried over anhydrous sodium sulfate. Toluene was evaporated under reduced pressure to give N-(4-chloro-α-methylbenzyl)-2,2-dichloro-1-methyl-(trans)-3-methylcyclopropanecarboxamide (29 g) represented by the following formula as colorless crystals. mp. 132°–134° C.

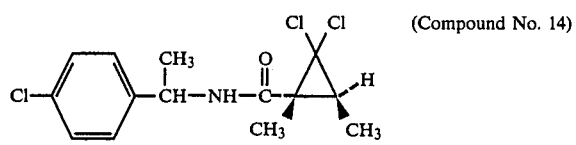 (Compound No. 14)

Table 4 below shows the compounds of this invention synthesized by the same procedure as in Example 14:

TABLE 4

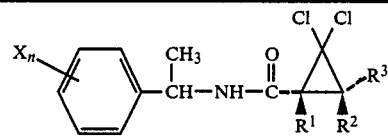

| Compound No. | $X_n$ | $R^1$ | $R^2$ | $R^3$ | Physical constant |
|---|---|---|---|---|---|
| 15 | 2-Cl | —CH₃ | H | H | mp. 161–162° C. |
| 16 | 4-Cl | —CH₃ | H | H | mp. 123–125° C. |
| 17 | 4-Cl | H | —CH₃ | H | mp. 124–126° C. |
| 18 | 3,4-Cl₂ | —CH₃ | H | H | mp. 140–142° C. |
| 19 | 4-Cl | H | —CH₃ | —CH₃ | mp. 132–133° C. |
| 20 | 4-Cl | —CH₃ | —CH₃ | —CH₃ | mp. 147–148° C. |
| 21 | 4-Cl | —C₂H₅ | H | H | mp. 135–138° C. |
| 22 | 4-Cl | H | —C₂H₅ | —C₂H₅ | |
| 23 | 4-Br | —CH₃ | —CH₃ | H | mp 126–128° C. |
| 24 | 4-Cl | —C₂H₅ | —C₂H₅ | H | |
| 25 | 4-Cl | —CH₃ | —C₃H₇—n | H | |
| 26 | 4-Cl | H | —C₄H₉—n | H | |
| 27 | 4-Br | —C₂H₅ | —C₂H₅ | —C₂H₅ | |
| 28 | 3,4-Cl₂ | —CH₃ | —CH₃ | H | mp. 138–139° C. |
| 29 | 4-Cl | —C₃H₇—n | H | H | mp. 131–132° C. |
| 30 | 4-Cl | —C₃H₇—i | H | H | |
| 31 | 4-Cl | —C₂H₅ | —CH₃ | H | mp. 168–170° C. |
| 32 | 4-F | —CH₃ | —CH₃ | H | mp. 127–129° C. |
| 33 | 4-Cl | —CH₃ | —C₂H₅ | H | NMR(60MHz) $\delta_{TMS}^{CDCl_3}$ 0.96~1.90 (m: 11H) 2.15 (t: 1H) 4.85~5.25 (m: 1H) 5.83~6.13 (m: 1H) 7.25 (s: 4H) IR(nujol)$\nu$(cm⁻¹) 1550, 1640, 3300 |

TABLE 4-continued

Structure: X_n-phenyl-CH(CH3)-NH-C(=O)-cyclopropane(Cl,Cl)(R1)(R2)-R3

| Compound No. | $X_n$ | $R^1$ | $R^2$ | $R^3$ | Physical constant |
|---|---|---|---|---|---|
| 34 | 4-Cl | —CH₃ | —C₃H₇—iso | H | mp. 145~147° C. |
| 35 | 4-Br | —CH₃ | —CH₃ | —CH₃ | mp. 150~151° C. |
| 36 | 4-Cl | —CH₃ | —C₂H₅ | —C₂H₅ | mp. 128~135° C. |
| 37 | 4-Br | —C₃H₇—iso | H | H | IR: $\nu$(cm⁻¹) 1520, 1635, 3300 |
| 38 | 4-Cl | —C₄H₉—sec | H | H | IR: $\nu$(cm⁻¹) 1520, 1650 3250~3300 |
| 39 | 4-Cl | —C₄H₉—iso | H | H | IR: $\nu$(cm⁻¹) 1525, 1625~1635 3270~3300 |
| 40 | 4-Cl | —C₂H₅ | —CH₃ | —CH₃ | mp. 94~98° C. |
| 41 | 4-Cl | —C₃H₇—iso | —CH₃ | H | |
| 42 | 4-Cl | —C₃H₇—iso | —CH₃ | —CH₃ | |
| 43 | 4-Br | —C₂H₅ | —CH₃ | H | mp. 208~210° C. |
| 44 | 4-Br | —C₃H₇—iso | —CH₃ | H | |
| 45 | 4-Br | —C₃H₇—iso | —CH₃ | —CH₃ | |
| 46 | 4-Cl | —C₂H₅ | H | —CH₃ | |
| 47 | 4-Br | —CH₃ | H | —CH₃ | |
| 48 | 4-F | —CH₃ | H | —CH₃ | |
| 49 | 4-Cl | —C₃H₇—iso | H | —CH₃ | |
| 50 | 4-Br | —C₂H₅ | H | —CH₃ | |
| 51 | 4-Br | —C₂H₅ | —CH₃ | —CH₃ | |
| 52 | 4-Cl | —CH₃ | H | —CH₃ | |
| 53 | 4-F | —C₃H₇—iso | H | H | mp. 103~105° C. |

REFERENTIAL SYNTHESIS EXAMPLE

Sodium trichloroacetate (55 g) was added to methyl 2-chloro-3-methyl-2-butenoate (15.5 g) at 100° to 120° C. over 5 hours. After the addition, the mixture was stirred further for 2 hours at the same temperature. After cooling, the reaction mixture was extracted with ether. The ethereal layer was washed with water, and dried over anhydrous sodium sulfate. Ether was evaporated under reduced pressure. The residue was distilled under reduced pressure to give the desired methyl 1,2,2-trichloro-3,3-dimethylcyclopropanecarboxylate (10.3 g) represented by the following formula. bp. 156°–159° C./23 mmHg

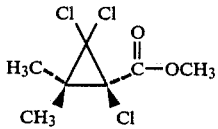

FORMULATION EXAMPLES

Wettable powder:

Fifteen parts of compound No. 1 of the invention, 80 parts of a 1:5 mixture of powdery diatomaceous earth and powdery clay, 2 parts of sodium alkylbenzenesulfonate/formaldehyde condensate are pulverized and mixed to form a wettable powder. It is diluted with water and sprayed onto a pathogen and/or the locus of its occurrence and the locus of occurrence of a crop disease.

Emulsifiable concentrate:

Thirty parts of compound No. 1 of the invention, 55 parts of xylene, 8 parts of polyoxyethylene alkyl phenyl ether and 7 parts of calcium alkylbenzenesulfonate are mixed with stirring to form an emulsifiable concentrate. It is diluted with water and sprayed onto a pathogen and/or the locus of its occurrence and the locus of occurrence of a crop disease.

Dust:

Two parts of compound No. 3 of the invention and 98 parts of powdery clay are pulverized and mixed to form a dust. It is scattered over a pathogen and/or the locus of its occurrence and the locus of occurrence of a crop disease.

Dust:

Compound No. 1 of the invention (1.5 parts), 0.5 part of isopropyl hydrogen phosphate (PAP) and 98 parts of powdery clay are pulverized and mixed to form a dust. It is scattered over a pathogen and/or the locus of its occurrence and the locus of occurrence of a crop disease.

Granules:

Water (25 parts) is added to a mixture consisting of 10 parts of compound No. 7 of the invention, 30 parts of bentonite (montmorillonite), 58 parts of talc and 2 parts of a lignosulfonate, and they are well kneaded. The mixture is processed by an extrusion-type granulating machine to form granules having a size of 10 to 40 mesh which are then dried at 40° to 50° C. to form granules. The granules are scattered over a pathogen and/or the locus of its occurrence and the locus of occurrence of a crop disease.

Granules:

Ninety-five parts of clay mineral particles having a particle size distribution between 0.2 and 2 mm are put in a rotary mixer, and with rotation, 5 parts of compound No. 1 of the invention dissolved in an organic solvent is sprayed onto the particles to wet them uniformly to form granules. They are then dried at 40° to 50° C. The granules are scattered over a pathogen and/or the locus of its occurrence and the locus of occurrence of a crop disease.

BIOLOGICAL EXAMPLES

Test for efficacy on rice blast by foliar application:

Preparation of a Test Compound

Active compound: 50 parts by weight

Carrier: 45 parts by weight of a 1:5 mixture of diatomaceous earth and kaolin

Emulsifier: 5 parts by weight of polyoxyethylene alkyl phenyl ether

The active compound, the carrier and the emulsifier in the amounts indicated above were pulverized and mixed to form a wettable powder. A predetermined amount of the wettable powder was diluted with water.

Testing Method

Rice plants (variety: Asahi) were grown in unglazed pots having a diameter of 12 cm. In the 3- to 4-leaf stage, a dilution of the test compound prepared above in a predetermined concentration was sprayed at a rate of 50 ml per three pots. On the next day, a suspension of artificially cultivated spores of *Pyricularia oryzae* was inoculated in the plants twice by spraying. The pots were maintained in a humid chamber having a relative humidity of 100% and a temperature of 25° C. to infect the plants. Seven days after the inoculation, the degree of disease was rated on the following standard, and the control index (%) was also calculated.

| Degree of disease | Percentage (%) of the area of lesion |
|---|---|
| 0 | 0 |
| 0.5 | 2 or less |
| 1 | 3-5 |
| 2 | 6-10 |
| 3 | 11-20 |
| 4 | 21-40 |
| 5 | 41 or more |

$$\text{Control index (\%)} = \frac{\text{Degree of disease of the non-treated area} - \text{Degree of disease of the treated area}}{\text{Degree of disease of the non-treated area}} \times 100$$

The results show an average of those obtained with three pots constituting one area. The results are shown in Table 5.

TABLE 5

| Compound No. | Concentration of the active ingredient (ppm) | Control index (%) |
|---|---|---|
| 1 | 250 | 100 |
| 2 | 250 | 100 |
| 14 | 250 | 100 |
| 16 | 250 | 100 |
| 19 | 250 | 100 |
| 20 | 250 | 100 |
| Comparison | | |
| A-1 | 250 | 0 |

TABLE 5-continued

| Compound No. | Concentration of the active ingredient (ppm) | Control index (%) |
|---|---|---|
| B-1 | 250 | 25 |

Note
Comparison A-1:

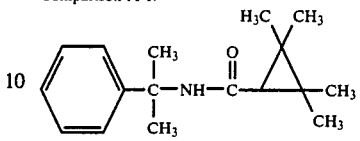

(the compound described in Japanese Laid-Open Patent Publication No. 66555/1980)

B-1:

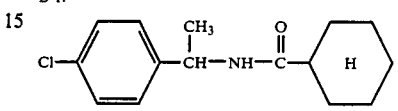

(the compound described in Japanese Laid-Open Patent Publication No. 26847/1983).

Other compounds of this invention than those shown in the above example were determined to exhibit nearly the same effects as shown in Table 5 in the same test.

Test for residual effect on rice blast:

Testing Method

Rice (variety: Asahi) was grown in unglazed pots having a diameter of 12 cm, and in the 3- to 4-leaf stage, a dilution of the test compound prepared as in Example 15 in a predetermined concentration was sprayed at a rate of 50 ml per three pots. Five days after spraying, a suspension of artificially cultivated spores of *Pyricularia oryzae* was inoculated in the plants twice. The pots were maintained in humid chamber having a relative humidity of 100% and a temperature of 25° C. to infect the plants. Seven days after the inoculation, the degree of disease per pot was rated as in Example 15, and the control index (%) was calculated. The results are shown in Table 6.

TABLE 6

| Compound No. | Concentration of the active ingredient (ppm) | Control index (%) |
|---|---|---|
| 1 | 250 | 100 |
|  | 100 | 100 |
| 6 | 250 | 100 |
|  | 100 | 100 |
| 8 | 250 | 100 |
|  | 100 | 100 |
| 14 | 500 | 100 |
|  | 250 | 100 |
| 16 | 500 | 100 |
|  | 250 | 100 |
| 19 | 500 | 100 |
|  | 250 | 100 |
| 20 | 500 | 100 |
|  | 250 | 100 |
| Comparison | | |
| A-1 | 500 | 0 |
| B-1 | 250 | 0 |

(Note):
Comparisons A-1 and B-1 are the same as in Table 5.

For example, compound No. 10, 23 and 24 were also determined to show an excellent residual effect in the same test as in this example.

Test for controlling anthracnose on cucumber:

Testing Method

A dilution of the test compound in the form of an emulsifiable concentrate prepared as described above in a predetermined concentration was sprayed onto cucumber (variety: suhyo) grown in 9 cm unglazed pots at a rate of 25 ml per three pots. One day after the spraying, a suspension of spores of *Collectotrichum lagenarium* was inoculated in the plants, and the pots were maintained for 1 day in a constant temperature chamber kept at 23° C. and a humidity of more than 90%.

Six days later, the degree of disease was rated by the percentage of the area of the lesion, and the control index (%) was calculated.

| Degree of disease | Percentage (%) of the area of lesion |
|---|---|
| 0 | 0 |
| 0.5 | 2 or less |
| 1 | 3–5 |
| 2 | 6–15 |
| 3 | 16–30 |
| 4 | 31–50 |
| 5 | 51 or more |

$$\text{Control index (\%)} = \frac{\text{Degree of disease of the non-treated area} - \text{Degree of disease of the treated area}}{\text{Degree of disease of the non-treated area}} \times 100$$

The results are shown in Table 7.

TABLE 7

| Compound No. | Concentration of the active ingredient (ppm) | Control index % |
|---|---|---|
| 1 | 500 | 100 |
| 2 | 500 | 100 |
| 14 | 500 | 100 |
| 18 | 500 | 100 |
| Comparison |  |  |
| TPN (commercial product) | 500 | 95 |

(Note):
TPM: tetrachloroisophthalonitrile, 75% wettable powder.

For example, compounds Nos. 12 and 24 were also determined to have an excellent controlling effect against anthracnose on cucumber in the same test as above described.

It is understood that the specification and examples are illustrative but not limitative of the present invention and that other embodiments within the spirit and scope of the invention will suggest themselves to those skilled in the art.

We claim:

1. An N-benzyl-cyclopropanecarboxamide of the formula

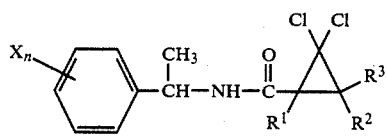

wherein
X represents halogen,
n represents 1 or 2,
$R^1$ represents hydrogen, halogen or lower alkyl,
$R^2$ represents lower alkyl, halogen-substituted lower alkyl or hydrogen, and
$R^3$ represents hydrogen or lower alkyl.

2. An N-benzyl-cyclopropanecarboxamide according to claim 1 wherein
X represents fluoro, chloro, bromo or iodo,
$R^1$ represents hydrogen, fluoro, chloro, bromo, iodo, or alkyl with 1 to 4 carbon atoms,
$R^2$ represents hydrogen, alkyl with 1 to 4 carbon atoms or halogensubstituted alkyl with 1 to 4 carbon atoms and 1 to 5 halogen atoms, and
$R^3$ represents hydrogen or alkyl with 1 to 4 carbon atoms.

3. An N-benzyl-cyclopropanecarboxamide according to claim 1, wherein
X represents fluoro, chloro or bromo,
$R^1$ represents hydrogen, methyl, ethyl, n-propyl, iso-propyl, chloro, bromo or fluoro,
$R^2$ represents hydrogen, methyl, ethyl, n-propyl, iso-propyl, n-butyl, tert.-butyl, sec.-butyl, iso-butyl, chloromethyl, bromomethyl, trifluoromethyl, 2,2,2-trifluoroethyl or 2-chloroethyl, and
$R^3$ represents hydrogen, methyl or ethyl.

4. An N-benzyl-cyclopropanecarboxamide according to claim 1, wherein such amide is N-(4-chloro-α-methylbenzyl)-1,2,2-trichloro-3,3-dimethylcyclopropanecarboxamide of the formula

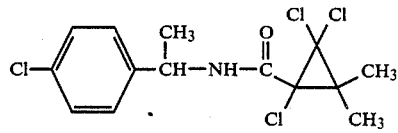

5. An N-benzyl-cyclopropanecarboxamide according to claim 1, wherein such amide is N-(4-chloro-α-methylbenzyl)-2,2-dichloro-3-chloromethyl-3-methyl-cyclopropanecarboxamide of the formula

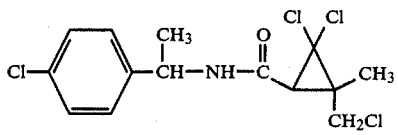

6. An N-benzyl-cyclopropanecarboxamide according to claim 1, wherein such amide is N-(4-chloro-α-methylbenzyl)-2,2-dichloro-1,3-dimethylcyclopropanecarboxamide of the formula

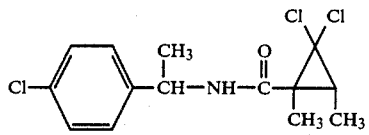

7. An N-benzyl-cyclopropanecarboxamide according to claim 1 of the formula

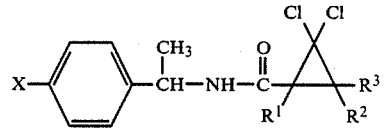

wherein

X represents chloro or bromo

R¹ represents alkyl with 1 to 4 carbon atoms and R² and R³ each independently is hydrogen or alkyl with 1 to 4 carbon atoms.

8. An N-benzyl-cyclopropanecarboxamide according to claim 1, wherein such amide is N-(4-chloro-α-methylbenxyl)-2,2-dichloro-1-ethyl)-3,3-dimethylcyclopropanecarboxamide of the formula

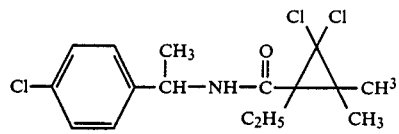

9. A fungicidal composition comprising a fungicidally effective amount of a compound according to claim 1 in admixture with a diluent.

10. A fungicidal composition comprising a fungicidally effective amount of a compound according to claim 7 in admixture with a diluent.

* * * * *